United States Patent [19]

Baugh

[11] 3,970,749

[45] July 20, 1976

[54] INTERFERON PRODUCTION

[76] Inventor: Clarence L. Baugh, 6608 Orlando Ave., Lubbock, Tex. 79413

[22] Filed: Apr. 3, 1973

[21] Appl. No.: 347,422

[52] U.S. Cl. ................................................ 424/85
[51] Int. Cl.$^2$........................................ A61K 45/02
[58] Field of Search .................................... 424/85

[56] References Cited
UNITED STATES PATENTS 3,039,932   6/1962   McLimans et al. ................. 195/1.8

FOREIGN PATENTS OR APPLICATIONS 960,769   6/1964   United Kingdom................... 424/85

OTHER PUBLICATIONS

Harris, *Techniques in Experimental Virology*, published by Academic Press, New York, 1964, pp. 337–339.

Finter, *Interferons*, published by North–Holland Publishing Co., Amsterdam, 1966, p. 35.

*Webster's New World Dictionary of the American Language*, College Edition, published by The World Publishing Co., New York, (1966), p. 232.

*Primary Examiner*—Sam Rosen
*Attorney, Agent, or Firm*—Berman, Aisenberg & Platt

[57] ABSTRACT

Animal tissue is trypsinized to form a cell suspension which is placed in a nutrient medium with a virus. Produced interferon is centrifugally separated, acidified and stored at a low temperature to inactivate the virus. It may then be frozen until it is prepared for use.

18 Claims, No Drawings

INTERFERON PRODUCTION

BACKGROUND OF THE INVENTION

Interaction of animal cells (of one animal species) with viruses produces a protein which can confer resistance to infection from a wide range of viruses on fresh animal cells of the same species. The protein is interferon.

Considerable is known about interferon, its preparation and activity, as reflected in "The Merck Index", eighth edition, page 568, Merck & Co., Inc., 1968, and "McGraw-Hill Encyclopedia of Science and Technology", third edition, volume 7, pages 221 and 222, 1971, and further references cited in these texts. Production of mouse interferon is described by Finter, N. B., Nature, Vol. 206, pages 597 to 599, May, 1965.

There are huge investments in fur-bearing animals, e.g. mink, and in domestic animals, such as cows, horses, swine and poultry, particularly meat-providing animals, which are subject to viral attack. Preventing or checking such viral attack would go a long way toward protecting such investments.

When a body receives a viral infection, the body, under normal, natural circumstances, produces interferon. This interferon spreads from one cell to adjacent cells or is circulated through the circulatory system throughout the body so the whole body is affected. Interferon operates to interfere with reproduction and spread of virus; thus, in effect, it checks or prevents viral infection.

Interferon is essentially species specific, but not virus specific. Interferon produced in one species of animal or in organs of one species of animal is essentially effective only in that species. However, interferon produced by the use of one virus has been found to be effective for preventing or checking the spread of many other viruses.

SUMMARY

The invention is directly concerned primarily with veterinary sciences. It is applicable to virtually all animal species, such as domestic animals, e.g. dogs and cats, but more specifically to livestock, e.g. cattle. Interferon is produced in body cells taken from an animal and thereafter extracted from such cells. Thus-produced interferon is administered to a living animal of the same species.

Organs of animals which are generally slaughtered for food are readily available from slaughterhouses. Such organs, particularly the spleen, serve as an excellent means for producing interferon. Any virus-culture-supporting animal tissue can be used for this purpose.

An object of the invention is to produce interferon suitable for protecting any animal from viral disease. A further object is to provide a source of tissue for interferon production which is readily available, inexpensive and capable of high yields. Another object is to produce interferon without employing a virus which will adversely affect the animal to which the interferon is administered. A still further object is to inactivate any employed virus prior to use of produced interferon. Other objects of this invention are to achieve the above with a method that is versatile, rapid, efficient, and inexpensive, and does not require skilled people to install, adjust, operate, and maintain.

The specific nature of the invention, as well as other objects, uses, and advantages thereof, will clearly appear from the following description.

DETAILED DESCRIPTION

The spleen of any animal, such as bovine spleen obtained, e.g., from a slaughterhouse, is removed from its capsule or outer covering so the parenchyma is reasonably free from bacteria and exterior contamination. Such spleen parenchyma is then finely chopped or minced and treated with trypsin to obtain trypsinized cells. The preceding steps are in accord with well-known established procedures.

Thus-trypsinized cells are placed in a nutrient solution or tissue cultrue medium so that cell concentration in the medium is about $10^7$ per milliliter (ml). A beaker is suitable for this procedure. Several readily available media are useful for this purpose, but Eagle's medium, preferbly Eagle's minimal essential medium, is recommended. Alternative media include Hank's balanced salt solution, Earl's balanced salt solution and Parker's medium No. 199.

The medium is inoculated with virus immediately after placing the cells therein. To minimize transmission or danger of any infection to the animal to be treated with prodced interferon, a virus which causes a disease specific to a different animal species is preferably selected. Thus, interferon prepared for bovine treatment is best produced with a virus which is specific to birds or other different species. Newcastle disease virus (NDV) is just such a virus. Moreover, it is particularly fruitful with regard to the amount of interferon proliferated in nutrient medium with trypsinized tissue cells.

About 5 ml of viral solution per liter (l) are added to the admixture of trypsinized cells and medium. This is within a range of from 10 to 100 virus particles for each spleen cell.

The resulting mass is gently stirred (according to standard operating procedures in the art) to prevent any separation of material (maintaining solids in suspension) and maintained at 37°C. A substantial interferon production is obtained after about 18 hours, at which time centrifugation is effected to remove solid material (composed primarily of spleen cells) from the thus-treated mass.

The centrifugate is acidified to lower its pH to two. This is accomplished with, e.g., 12 N hydrochloric acid. The acidified centrifugate is stored for 7 days at 5°C. The 7 days of storage at low temperature and pH inactivates the virus. At the end of this storage period, it is exposed for about two minutes to ultraviolet radiation in a thin, shallow tray. The exact procedure with ultraviolet radiation to eliminate bacterial contamination may be varied according to standard laboratory techniques. The product is then frozen at −20°C for subsequent use. It can be stored up to one year, or more.

To use, suxh frozen product is thawed and injected either cold or at body temperature. At the present time, injections of 25cc into an animal having a body weight of approximately 300 pounds, plus or minus 100 pounds, are made. However, circumstances may warrant different dosages.

It is essential that the cells be maintained in suspension in a culture medium. Cells, other than certain tumor-producing cells, taken directly from animal tissue will not grow in this type of suspension. The process neither provides for nor requires cells to attach to a solid surface, e.g. glass; moreover, no growth period (for cells in nutrient or culture medium) is necessary or permitted before a virus or inducer is introduced and interferon produced. The suspension method makes the process economically feasible and minimizes risk of bacterial contamination.

As previously indicated, even though many viruses can be used, the selection of a foreign-host, i.e. non-host, virus (one which is specific to an animal species different from that to be treated with obtained interferon) is one of the easiest ways to safeguard against a severe viral infection in the treated animal. A rapidly-multiplying virus is also most desirable from the standpoint of both economy and production. NDV satisfies both of these criteria for the production of interferon for bovine use. Embryonated eggs are used to produce NDV. According to standard laboratory procedures, the embryo is prepared by removing the head and feet; the embryo is then finely chopped, and the cells are separated by trypsinization. The trypsinized cells are placed in Eagle's minimal medium and seeded with NDV. The concentration of the trypsinized cells in the medium is $10^7$ per ml. The embryo cells are then infected or seeded with 5 ml/l (within the range of from 10 to 100 virus particles per embryo cell) of virus. Twenty-four hours after seeding, during which time the seeded medium is maintained at 37°C and gently agitated to prevent separation, the viral production is complete. After the viral production is complete, it is centrifuged and the centrifugate is the source of the virus which is used to add to the interferon beaker.

Animal tissue other than apleen is useful for interferon production according to the previously-described procedure. In fact any animal tissue on which a selected virus can be cultured is useful for this purpose. However, there are material advantages to the use of spleen; it is readily available; it is low in price; and it yields high amounts of interferon on maintenance culture, i.e. as opposed to culture on growing cells. Such other animal tissue includes, e.g., kidney tissue and testes; spleen tissue is preferred.

The disclosed procedure is also not limited to the production of bovine interferon. Interferon for, e.g., horses, swine, dogs or poultry is similarly produced. In producing interferon for poultry, a virus which does not affect poultry is preferably selected.

As interferon is species specific, that which is produced from bovine spleen is useful for, e.g., cows and oxen, whereas that produced from hog spleen is useful for swine. Appropriate interferon, i.e. that produced with tissue of the animal species to which it is to be administered, is ordinarily administered by subcutaneous injecion. However, it can be sprayed topically on infected areas for certain eye infections, e.g. pink eye, for which it appears to have therapeutic value as well as prophylactic value.

All livestock is susceptible to viral attack, and such attack can be prevented or minimized by prompt administration of interferon to exposed animals.

Injections of interferon are primarily of prophylactic value. It is of value for new-born pigs and might be introduced orally inasmuch as the intestines absorb proteins (interferon is a protein) for a period of time post partum; therefore, interferon can be administered within 30 minutes or an hour after birth. It is particularly useful in this case for preventing attack by intestinal viruses.

Generally, the effects of an interferon injection last from 4 to 6 days.

Interferon is primarily used to prevent viral infections or prophylactically; therefore, it is ordinarily administered at the time the animal is particularly susceptible to viral infection. In pigs exposed to enterovirus, this is within an hour of birth; in cattle, increased susceptibility to virus infection occurs shortly after shipping.

The embodiment described above is only exemplary. I do not claim to have invented all the parts, elements or steps described. Various modifications can be made in the material, arrangement, and operation, without exceeding the scope of the invention. The limits of the invention and the bounds of patent protection are measured by and defined in the following claims. The restrictive description of the specific example above does not point out what an infringement of this patent would be, but is to enable the reader to make and use the invention.

What is claimed is:

1. A method of producing interferon which comprises:
   a. inoculating with virus a suspension of virus-culture-supporting animal cells, taken directly from trypsinized normal animal tissue, in a nutrient or culture medium without permitting an intervening growth period for the cells in the suspension,
   b. maintaining the resulting virus-inoculated suspension in the nutrient or culture medium of virus-culture-supporting animal cells at least until interferon is produced therein, and
   c. centrifuging the interferon-containing composition to remove solids therefrom and to collect interferon in thus-obtained centrifugate.

2. In a process for producing interferon for an animal, the improvement which comprises a method according to claim 1 wherein the animal tissue cells are spleen cells of a species to which the animal belongs.

3. A method according to claim 2 for producing interferon for livestock.

4. A method according to claim 2 wherein the virus is a non-host virus.

5. A method according to claim 4 which further comprises inactivating virus in the centrifugate.

6. A method according to claim 5 wherein the spleen cells are those of cattle.

7. A method according to claim 6 wherein the spleen cells are bovine spleen cells.

8. A method according to claim 6 wherein the spleen cells are swine spleen cells.

9. A method according to claim 5 wherein the nutrient medium is Eagle's medium.

10. A method according to claim 9 wherein the (nutrient medium)/(spleen cell) composition has a concentration of $10^7$ spleen cells per milliliter.

11. A method according to claim 10 wherein the spleen cells are those of cattle and the non-host virus is Newcastle disease virus.

12. A method according to claim 11 wherein the non-host virus-inoculated composition is maintained for eighteen hours for interferon production therein.

13. A process according to claim 12 which comprises acidifying the centrifugate to a pH of 2.

14. A method according to claim 13 wherein the virus is inactivated by chilling the acidified centrifugate to 5°C and maintaining it at that temperature for seven days.

15. A method according to claim 14 wherein the spleen cells are bovine spleen cells.

16. A method according to claim 14 wherein bacterial contamination is eliminated by exposing inactivated-virus-containing centrifugate to ultraviolet irradiation.

17. A method according to claim 14 which comprises freezing and storing virus-inactivated centrifugate.

18. In a method of producing interferon which comprises inoculating virus-culture-supporting animal cells with a virus in a nutrient or culture medium, maintaining the resulting virus-inoculated cells in the nutrient or culture medium at least until interferon is produced therein and collecting thus-produced interferon, the improvement wherein critcal features consist essentially of:

a. the virus-culture-supporting animal cells are taken directly from trypsinized normal animal tissue;

b. the virus-culture-supporting animal cells are in suspension when inoculated with the virus and during interferon production; and c. the virus-culture-supporting animal cells are inoculated with the virus without permitting an intervening growth period for the cells in suspension.

* * * * *